US006402745B1

(12) United States Patent
Wilk

(10) Patent No.: US 6,402,745 B1
(45) Date of Patent: Jun. 11, 2002

(54) INTRAVENOUS WHIP ELECTRODE FOR VEIN ABLATION

(76) Inventor: Peter J. Wilk, 185 West End Ave.-Unit 22M, New York, NY (US) 10023

( * ) Notice: Subject to any disclaimer, the term of this patent is extended or adjusted under 35 U.S.C. 154(b) by 0 days.

(21) Appl. No.: 09/511,615

(22) Filed: Feb. 23, 2000

(51) Int. Cl.[7] .......................... A61B 18/04; A61B 17/22
(52) U.S. Cl. .......................... 606/41; 606/27; 606/32; 606/157; 606/158; 606/159
(58) Field of Search .......................... 606/41, 157, 158, 606/159

(56) References Cited

U.S. PATENT DOCUMENTS

| | | | |
|---|---|---|---|
| 4,418,692 A | * 12/1983 | Guay | 606/42 |
| 4,677,990 A | * 7/1987 | Neubauer | 607/119 |
| 4,869,248 A | * 9/1989 | Narula | 606/29 |
| 5,267,982 A | * 12/1993 | Sylvanowicz | 604/281 |
| 5,437,664 A | * 8/1995 | Cohen et al. | 606/42 |
| 5,673,695 A | * 10/1997 | McGee et al. | 606/41 |
| 5,709,224 A | * 1/1998 | Behl et al. | 606/41 |
| 6,146,395 A | * 11/2000 | Kanz et al. | 606/159 |
| 6,162,219 A | * 12/2000 | Nilsoon et al. | 606/41 |
| 6,200,312 B1 | * 3/2001 | Zilorus et al. | 606/32 |
| 6,200,315 B1 | * 3/2001 | Gaiser et al. | 606/41 |

* cited by examiner

Primary Examiner—Lee Cohen
Assistant Examiner—H. M. John, III
(74) Attorney, Agent, or Firm—R. Neil Sudol; Henry Coleman; William Sapone

(57) ABSTRACT

An intravenous surgical instrument comprises an inner shaft or post and an outer sheath. At a distal end of the inner post or post a spring-tail or whip-like electrode is disposed substantially in a sagittal plane, or one perpendicular to a longitudinal axis of the shaft. Following an insertion into a human vein or other circulatory vessel the distal end of the shaft is protruded from the sheath; thereafter sheath, post and electrode are simultaneously withdrawn from the vein, with a relative rotatory motion being imparted to the electrode. A current flow is preferably simultaneously imposed across the electrode into an inner surface of the surrounding vessel, facilitating a damaging of the vessel inner surface and a collapse of the vessel. This description applies primarily to veins, which may be drained of blood prior to a start of a collapsing procedure; for use in arteries a modified embodiment is disclosed employing a compound construction electrode tip which facilitates a limiting of current flow to a region of direct electrode contact with a circulatory vessel wall, and a reduction of stray currents conduction into the blood.

18 Claims, 2 Drawing Sheets

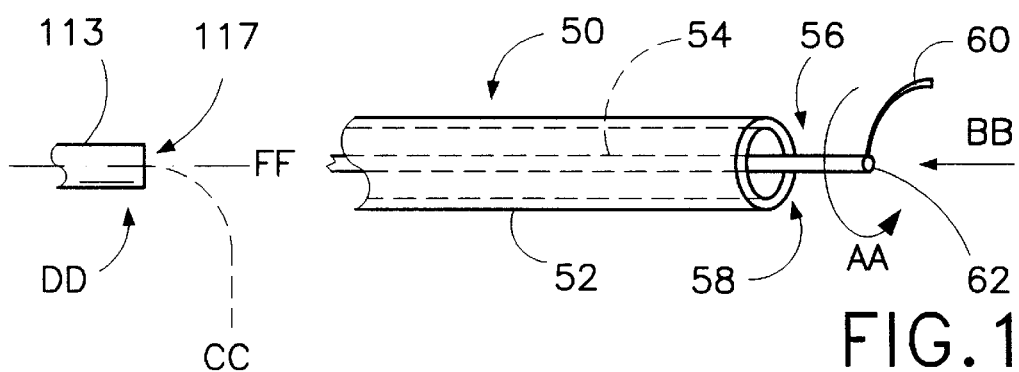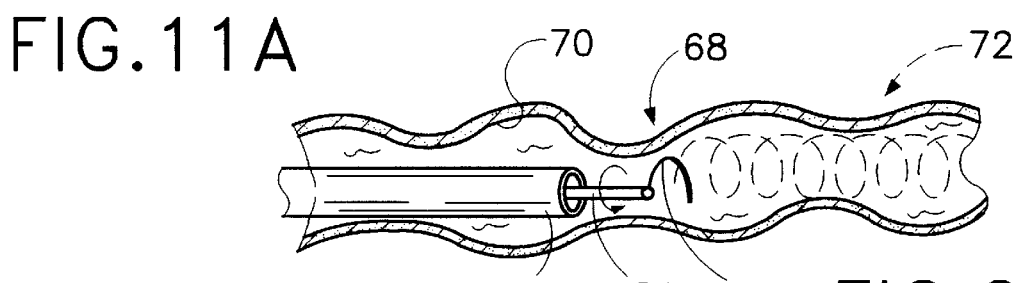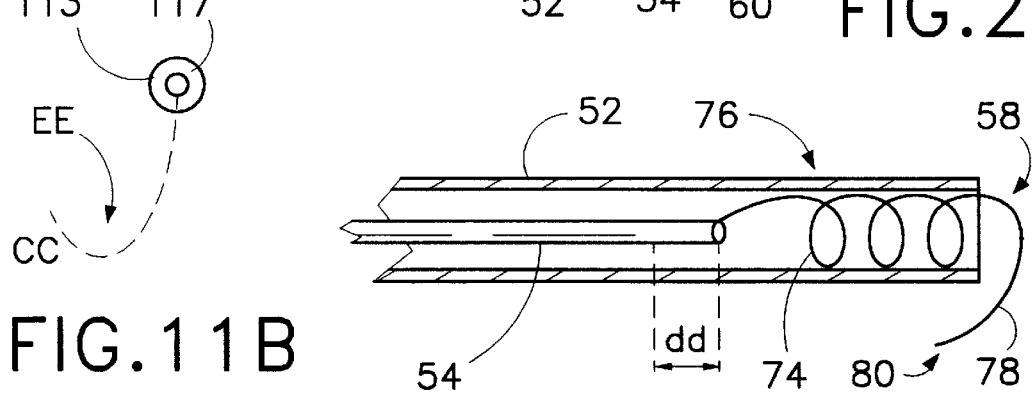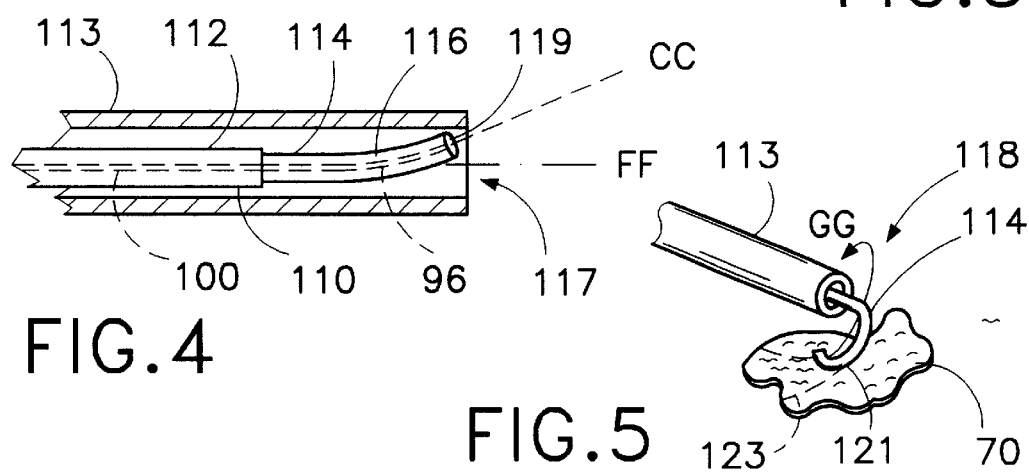

INTRAVENOUS WHIP ELECTRODE FOR VEIN ABLATION

BACKGROUND OF THE INVENTION

This invention relates to a method for treating a varicose vein. More particularly, this invention relates to a method for eliminating a varicose vein. This invention also relates to an associated device for use in the method.

In varicose veins, the valves are malfunctioning or destroyed so that the veins balloon at the lower ends. This condition can be particularly pronounced in certain leg veins. In a conventional surgical procedure for the treatment of varicose veins, two incisions are made in a vein, one at the ankle and one at the groin. An elongate stripper instrument is then inserted through the ankle incision and passed through the vein to the groin. At the groin, a cup is attached to the distal end of the stripper. Subsequently, the stripper is pulled down the leg so that the cup rips out the vein.

In this procedure, other veins connecting to the varicose vein are torn. The leg subsequently turns ugly shades of black and blue. Of course, the patient experiences substantial pain and suffering from the procedure.

Various means have been proposed to eliminate or close varicose veins with less surgical trauma, including damaging an inner endothelial surface of a vein with laser, electric or radio-frequency energy. Motivation for such damage is the known tendency of internally damaged circulatory vessels to collapse and remain collapsed through adhesion of damaged or mutilated surfaces; essentially a beneficial application of otherwise undesirable or post-surgical adhesion. Known means to achieve endothelial damage however generally suffer from a drawback that the intensity of energy imparted to the endothelial surface is uneven, particularly so when the vein is irregular in cross-section, and the diameter varies over a treated length.

OBJECTS OF THE INVENTION

An object of the present invention is to provide a method for treating varicose veins.

Another object of the present invention is to provide such a method which results in less pain to the patient than the conventional technique.

An additional object of the present invention is to provide such a method which generates less hematoma than the conventional technique.

A further object of the present invention is to provide such a method wherein injury to the nerves is reduced.

Yet a further object of the invention is to provide a method and device for delivering a similar treatment to arteries.

These and other objects of the present invention will be apparent from the drawings and \ed descriptions herein.

SUMMARY OF THE INVENTION

A medical method for collapsing circulatory vessels in vivo in accordance with the present invention utilizes an elongate element having an at least partially flexible appendage attached to a tip of the element. The method comprises inserting said elongate element and said appendage in a circulatory vessel of a patient and then simultaneously rotating and withdrawing the elongate element from the blood vessel, causing the appendage to describe an essentially helical contact path with an inner surface of the vessel, to thereby damage the inner surface and facilitate a permanent collapse of the vessel.

In accordance with a particular embodiment of the present invention, the appendage takes the form of a whip-like surgical steel spring or spring-tail wire component of an intravenous surgical instrument and is disposed inside the vein or other elongate circulatory vessel in a sagittal plane thereof. The wire or spring-tail is attached at a first end to a central post or shaft of an elongate tool inserted in the vein, and coils outward in the sagittal plane, substantially perpendicular to a longitudinal axis of the elongate vessel. A second end of the spring-tail is free, and tangentially and pressingly disposed along an inner surface or endothelium of the vein. During a withdrawal of the instrument the shaft is simultaneously rotated and pulled from the vessel, and the second end of the spring-tail is drawn over the endothelium in a helical or spiral pattern in which the endothelium is scored or damaged. By a proper choice of size and relaxed shape of the spring-tail, the spring-tail remains in continuous contact with the endothelium during the withdrawal with approximately constant contact area. Therefore a relatively uniform amount of damage is done to the inner vessel walls during the withdrawal operation.

In the context of this disclosure, a "spring-tail" may be taken explicitly to mean a short wire-element, thin enough in cross-section, and of sufficient stiffness, to withstand a significant bending strain without plastic deformation. In other words, a spring-tail is an object having the mechanical properties of a section of a coil spring having an arcuate form elastically deformable between a straight configuration on one hand and approximately a full turn of coil on the other hand.

In a second particular embodiment of the present invention, the shaft is disposed within an first insulated sheath, electrically isolating the shaft from an inner surface or wall of the vessel. The spring-tail in this embodiment serves as a first electrode, a second electrode being disposed outside of a patient, possibly in a form of a grounding strip. A current path then exists along the central post or shaft, passing through the spring-tail or first electrode, through a contact point between the first electrode and an inner wall or endothelium of the circulatory vessel, and thence diffusely to an outer surface of the patient. The contact point between the first electrode and the endothelium thereby forms a most restricted, and therefore highest resistance, portion of the current path passing through fleshy part of the patient. Consequently, a highest concentration or intensity of cellular damage attributable to current flow is realized at the contact point with the endothelium.

While a degree or concentration of damage in cells of the endothelium is enhanced by the passage of current, over purely mechanical means, a drawback of this embodiment inheres in the conductivity of human blood, which comprises a saline solution, and a resultant dilution of a contact current density by a blood borne current. This limitation is overcome or compensated in a third embodiment of the present invention. In this embodiment, a modified, composite, first electrode includes a second sheath surrounding the spring-tail. The sheath is fabricated of a high-resistance alloy, such as would be suitable for thin film heater elements, and is insulated from the tail when in a relaxed or non-deformed configuration by either an air-gap, or a filling of a non-conductive gel, such as a petroleum jelly. When pressed against an inner surface or wall of a vessel, the sheath of the composite electrode deforms by design with marginally less stiffness than the tail, and as a result the sheath and tail are brought into an internal contact in an area of contact of the second sheath with the inner wall, as more fully described hereinafter with reference to the drawings.

It will be appreciated that in a thin film of high-resistance alloy conduction is more facile across a thickness of the film than along a surface direction. Accordingly, following a deformation of the composite electrode when pressed against a vessel wall, a substantial portion of the current will pass perpendicularly across the film and into the vessel wall, and a minor portion of the current will flow along a surface direction, and leak into surrounding blood. A degree of resistive heating will also be realized in the area of contact of sheath with the inner wall, and accordingly an enhanced degree of local cellular damage.

In case it is possible to empty a blood or circulatory vessel to be collapsed, as for example in the case of veins, the second embodiment will be seen to function optimally, without the appearance of leakage currents in the blood. In case the vessel cannot be drained, as is likely in the case of arteries, it will be seen that a utilization of the more complex third embodiment is indicated.

In yet another embodiment of a vascular surgical tool in accordance with the present invention, a modified form of the second embodiment, an electrode predisposed in a hollow version of the central post or shaft is compressively coiled inside the shaft. Upon being advanced toward a distal end of the shaft, a tip of the electrode emerges therefrom and partially uncoils, forming a spring-tail configuration lying in the sagittal plane of the circulatory vessel. Following a endothelium debriding operation, the partially uncoiled electrode tip may be snipped from the tool, preparatory to exposing a fresh surface in a subsequent operation. This method of feeding a spring or wire from a central shaft has application to both a purely mechanical and an electrically facilitated abrasion of the endothelium. A different mode of deployment is contemplated in the embodiment including a conducting sheath surrounding the spring-tail, or electrode tip. In this embodiment, the electrode tip and surrounding sheath are inserted into a vein or other vessel constrained by a first sheath to lie in generally a longitudinal axis of the vessel. Prior to commencement of a abrasion operation, a relative movement of a central post or shaft and the surrounding first sheath expels the electrode tip and sheath, which components are biased towards and then assume an arcuate conformation, lying generally at right angles to the central shaft, and in the sagittal plane.

BRIEF DESCRIPTION OF THE DRAWINGS

FIG. 1 is a schematic perspective of an intravenous surgical instrument in accordance with the present invention.

FIG. 2 is a schematic cross section of a human vein or artery, showing an insertion and a mode of employment of the surgical instrument of FIG. 1.

FIG. 3 is a cross-sectional view of a modification of the instrument of FIG. 1.

FIG. 4 is a cross-sectional view of an alternative modification of the instrument of FIG. 1.

FIG. 5 is a schematic perspective, showing a mode of employment of the modified surgical instrument of FIG. 4 against an endothelial wall or inner surface of a human vein or artery.

FIG. 11A is a projection of an axis of a distal tip of the instrument of FIG. 4 in a plane containing a major longitudinal axis of the instrument.

FIG. 11B is a projection of an axis of a distal tip of the instrument of FIG. 4 in a plane perpendicular to a major longitudinal axis of the instrument.

DETAILED DESCRIPTION OF THE PREFERRED EMBODIMENTS

Figure 6:
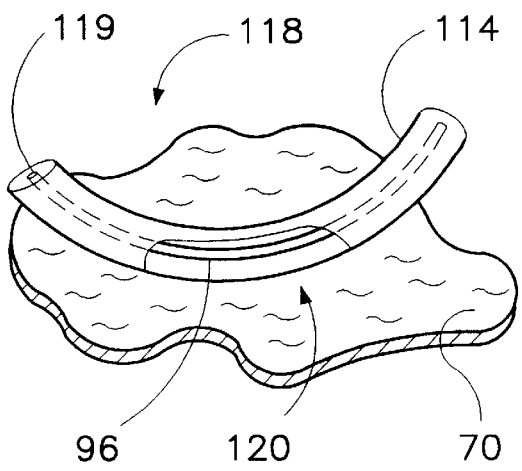
FIG. 6 is yet another schematic perspective, showing an active tip of the modified surgical instrument of FIGS. 4 and 5, partially in cut-away view, in contact with a wall or inner surface of a vein or artery.

As illustrated in FIG. 1, a surgical instrument 50 for use in effectuating the permanent collapse of tubular organs such as blood vessels comprises an outer tube or sheath 52 which substantially encloses an inner shaft or rod 54. A tail or end-section 56 of rod 54 may be alternately protruded and withdrawn through a distal mouth 58 of the sheath, the protrusion or withdrawal being controllable from a proximal end of the surgical instrument. A flexible appendage in the form of a whip-like spring or spring-tail wire lead 60 is mounted on a tip 62 of rod 54. The term "spring tail," defined in detail above, refers to a wire segment with the mechanical properties of a short segment of a coil spring, although, possibly straight in a relaxed conformation. The term "whip-like" may be construed identically in this context, with an implied reference to so-called whip antennas.

Figure 7:
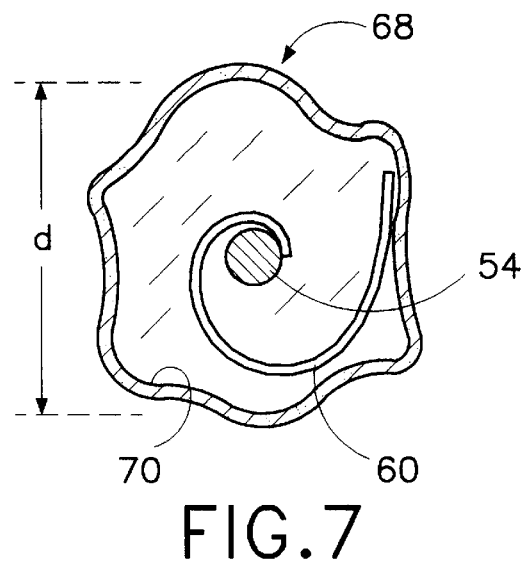
FIG. 7 is a schematic cross section of a human vein containing the instrument of FIG. 1.

Lead or spring-tail 60 has an arcuate form, as shown in FIG. 1, and, in a pre-loaded configuration (not shown) is withdrawn inside mouth 58, in a coiled configuration, along with the rod tail 56. An intended mode of use of instrument 50 is indicated by arrows AA and BB, signifying a rotation and simultaneous withdrawal of rod 54 relative to a human vein 68 in which the surgical device has been inserted (FIG. 2). As shown in FIG. 2, sheath 52 is simultaneously withdrawn from vein 68 along with rod 54 while the rod is being rotated. Rod 54 rotates relative to sheath 52 and with respect to an inner surface or endothelial layer 70 of the vein. In a relaxed or stationary extended configuration in vein 68, spring-tail 60 is disposed in a generally circumferential configuration, as shown in FIG. 7. Upon withdrawal and rotation of rod 54, a locus or path of contact of spring-tail 60 with the inner surface or endothelial layer 70 of vein 68 will have a generally helical conformation, as shown in FIG. 2.

Figure 8:
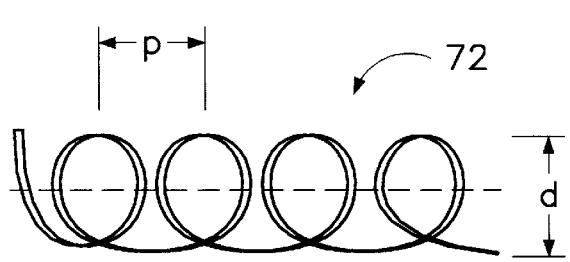
FIG. 8 is a geometric diagram illustrating characteristics of a helix.

Helix 72 has a pitch p (FIG. 8) determined both by a both a linear rate of withdrawal of rod 54 and a rate of angular rotation. Where rod 54 translates along a vein at a velocity v and with r rotations per unit time, the pitch p is equal to v/r, irrespective of an intravascular diameter d (FIGS. 7 and 8). Similarly, depending on intravascular diameter d and on instrument dimensions, control may be simultaneously effectuated over the dwell (the amount of time the wire lead is in contact with the endothelium while riding along the path or helix 72), spacing or pitch p, and in an embodiment where electric current is also employed, as discussed below, an electric current j. Thereby a degree of damage to the endothelium may be accurately controlled and a complete vein closure and collapse without wall breakthrough facilitated.

A second, alternative, embodiment of an intravenous surgical instrument is shown in FIG. 3. Attached to rod 54 is an appendage in the form of extended spring or mechanical lead 74 predisposed in a distal end 76 of sheath 52. In a deployment of the lead, following an insertion of the instrument into a circulatory vessel (not shown), rod 54 is advanced a predetermined distance dd, similar to an operation of the embodiment of FIG. 1, to expose a length of wire or spring-tail 78 at mouth 58 of the sheath. Contrary to a mode of operation of the embodiment of FIG. 1, however, only a portion of the lead or spring is exposed at mouth 58, a remaining portion staying inside the sheath following the deployment. Relative longitudinal or axial positions of rod 54 and sheath 52 are then locked at a proximal end of the instrument by any means (not shown) which will be apparent to those skilled in the relevant mechanical arts, in a manner which still allows relative rotation of the rod and the sheath.

At least two modes of employment of the embodiment of FIG. 3 are contemplated. In cases where a diameter of vein 68 changes significantly over a length of intended collapse, exposed wire 78 may be paid out or withdrawn over a course of an operation, in compensation for the varying diameter, thereby maintaining an approximately constant degree of intensity of damage to the endothelium. Separately, when a tip 80 of lead 74 becomes eroded or worn, a region (not designated) adjoining the tip may be trimmed, and a fresh length of wire 74 be exposed at mouth 58 for the execution of subsequent operations. A replacement cost of the tip or spring tail may hereby be reduced relative to the embodiment of FIG. 1.

The detailed embodiments discussed above contemplate a purely mechanical mode of damaging intravascular endothelium. An efficiency of tissue destruction, and hence vein collapse, may be increased by a passage of electric current through a rotating wire appendage or electrode and over the endothelial interface simultaneously with a rotation and withdrawal of the electrode. A design of an intravenous surgical tool for collapsing veins is schematically depicted in FIG. 9.

A D-C current source 82 is connected to a head or control unit 84 of an intravenous surgical instrument (not separately designated). Head 84 incorporates a mechanism for rotation, withdrawal, and relative movement of an outer sheath 86 and an inner post or flexible stalk 88. Sheath 86 is inserted through a break in a patient's skin (not shown) into a vein 90. At a distal end of the instrument, an electrode appendage 92 in a shape of a spring-tail or partially uncoiled spring section is provided. Electrode appendage 92 is disposed, in an inserted condition prior to commencement of tissue destruction, against an inner vessel surface or endothelium, similarly to the instrument deployment shown in FIG. 7. A return current path is provided from the patient either in a form of a connection 94 from tissue 95 to ground, possibly in a form of a grounding strap or electrode securely attached to wrist of ankle with an intervening layer of conductive paste, as known in the art, or in a direct current return to the power supply (not shown).

A trigger or other actuating mechanism (not shown) may be operatively connected to head or control unit 84 for simultaneously commencing a current supply, a rotation and a controlled withdrawal at pre-determined rates. The rates and various fine control steps, as necessary, for example, for the above described ejection of the electrode tip from the mouth of the sheath, may be set or controlled by appropriate individual controls (none shown). In accordance with standard laboratory techniques, a current source may either be set for constant current, or constant voltage, or some more complicated digitally controlled profile of either current or voltage, and a rotation and withdrawal may either be set for constant torque or force, respectively, or constant rotation and withdrawal rates, within a set range of torque or force. A pre-determined range of motion may also be set, allowing a automatic stop after a pre-selected length of vein collapse. These and other optional features will be evident to those skilled in the appropriate electrical and mechanical arts, and are disclosed to the public for completeness, without in any way being taken to limit the scope of the invention as delimited in the claims. It will also be appreciated by those skilled in the art that an A-C, or more complicated pulsed or digitally controlled power supply, may be substituted for a simple regulated D-C supply.

Figure 9:
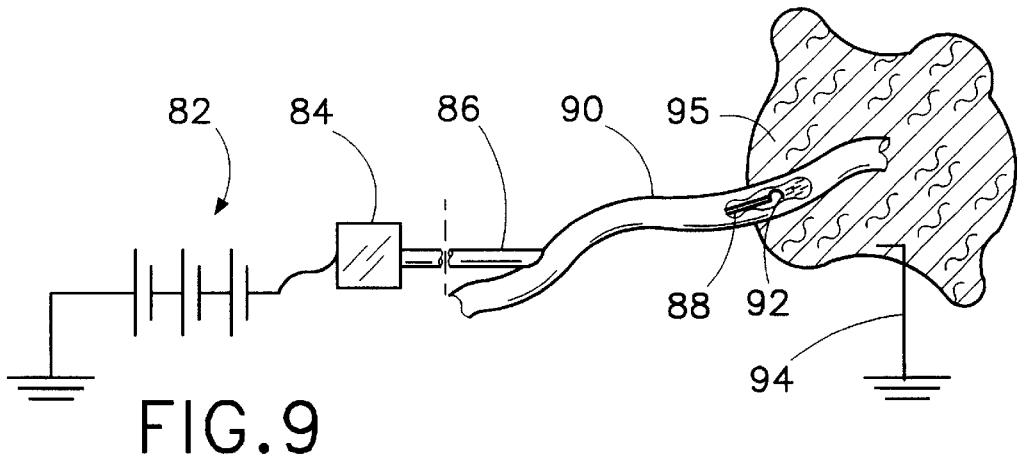
FIG. 9 is partially a perspective view, partially a circuit diagram and partially a cross-section of an deployed intravenous electrical surgical instrument in accordance with the present invention.

In an employment of the embodiment of FIG. 9, a length of vein (not designated) is clamped and drained of blood prior to commencement of an operation to collapse that vein. The primary motivation for this draining, in addition to a facilitation of a collapse and adhesion of a drained, pre-collapsed or air-filled vessel, is elimination of blood-borne conduction, which otherwise serves as a parasitic current tap for current desirably injected into a vessel wall, and makes an electrically assisted method of endothelial destruction inefficient or impractical.

In the case of drained vessels, the embodiments of FIG. 1, 2, 3 or 7 which include an un-insulated tail or tip of a central electrode disposed intravenously, are suitable for electrification. In the case of an artery, however, contained blood cannot be drained from a target length of vessel because of the superior arterial pressure, and an alternative embodiment must be employed. An embodiment suitable for intra-arterial endothelial destruction is shown in FIGS. 4, 5 and 6.

A third embodiment of an intravascular surgical instrument, as shown in FIG. 4, is suitable for employment in an undrainable vessel, such as a blood-filled artery. A spring-tail inner electrode 96 is attached in-line to a distal tip 98 of a shaft 100. Shaft 100 is enclosed in a first inner sheath 112 which is in turn enclosed in an outer sheath 113 functionally similar to sheath 52 of FIG. 1.

Figure 10:
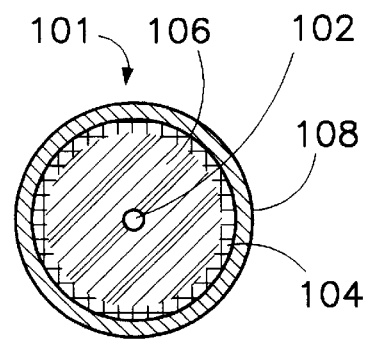
FIG. 10 is a cross-section of a co-axial electrical cable.

Shaft 100 optionally takes a form of a co-axial cable or conductor 101 (FIG. 10) having a center conductor 102 conductively connected to electrode 96 and an outer conductor 104 conductively connected to ground at a proximal end thereof, but not otherwise actively functioning as a circuit element. Outer conductor 104 is generally of a braided construction while inner or center conductor 102 is solid. Inner and outer conductors 102 and 104 are separated by an insulating layer 106, generally fabricated of nylon, while cable 101 is in toto sheathed in an elastomeric insulating jacket 108.

In the alternative, thinner construction, shaft 100 is replaced by a shaft of solid fabrication (not shown), lacking first inner sheath 112. Inn that event, a layer of insulating lubricant is utilized in concentric annular space 110 to limit blood entry and current conduction in an interior of sheath 113.

Completing the embodiment of FIG. 4, a second sheath 114 forms a termination of shaft 100. Sheath 114 and electrode 96 together form a short section of co-axial conductor or cable, with inner and outer conductors formed by the electrode and the sheath, respectively. Inner electrode 96 is terminated and centered at an insulating end-cap 119 of sheath 114. An annular space 116 intervening between electrode 96 and sheath 114 may be maintained as an air-gap, or optionally filled with a non-conductive gel (not shown), such as petroleum jelly, or other fluidic insulator material known in the art. Outer electrode or sheath 114 is sealed to elastomeric insulating jacket 108, when employed, or to a solid shaft, but is otherwise electrically isolated from remaining components of the intravenous surgical instrument.

Both sheath 114 and electrode 96 are of sufficient stiffness and thinness to undergo a significant degree of bending without plastic deformation. Sheath 114 and electrode 96 together form a tail-assembly or appendage 118 (FIG. 5) and have a relaxed or rest configuration (not designated) which may be characterized by a shape of a curvilinear central axis CC. Axis CC may be taken as coincident with electrode 96 and has a shape which may be comprehended from an inspection of FIGS. 5, 11A, and 11B.

In a deployed configuration shown in FIG. 5, tail assembly 118 first takes a bend DD (FIG. 11A) of approximately 45° to 90° with respect to a central longitudinal axis FF of outer sheath 113. Subsequently, moving along axis CC from the mouth 117 of sheath 113, a second bend EE of approximately 45° (a right angle is shown) or greater is taken in a plane approximately perpendicular to axis FF. A net effect or resulting conformation from bends DD and EE on tail-assembly 118 is shown in perspective in FIG. 5. The conformation of tail assembly 118 allows a smooth rotation of the assembly about axis FF, as indicated by arrow GG, while in contact with an inner wall or endothelium 70 of a circulatory vessel. A contact region 121 is, in operation, drawn along a substantially helical path 123. In a pre-deployment configuration of the tail-assembly or compound electrode 118, shown in FIG. 4, the assembly is disposed in a strained or elastically deformed configuration inside mouth 117 of sheath 113. Following an insertion of sheath 113 into an artery or other circulatory vessel, a distal movement of shaft 100 relative to the sheath ejects or protrudes tail assembly 118, allowing the assembly to relax into the configuration of FIG. 5. In this deployed configuration, tail assembly 118 is subject to deflection only by contact with inner wall or endothelium 70 of the circulatory vessel. This deflection is utilized to actuate and localize a current flow across the endothelium, as discussed below. A simplified version (not illustrated) of the third embodiment modifies tail assembly or "pig-tail" 118 to have a relaxed configuration substantially similar to a rest configuration of spring-tail 60 in FIG. 1, which pig-tail may in turn be either predisposed circumferentially in an outer sheath similar to sheath 52 for an insertion into an artery, or inserted without outer cover. These and other variations will occur to the practitioner skilled in the art, without departing from the spirit of the embodiment.

In another feature of embodiment of FIGS. 4 and 5, inner conductor or electrode 96 and outer conductor or sheath 114 are configured to maintain the annular space or gap 116 while in the relaxed or rest configuration shown in FIG. 5. Upon deflection by an arterial wall or endothelium 70, however, inner electrode 96 makes contact with an inner surface (not designated) of sheath 114 in a region of the deflection. Sheath 114 is fabricated of a conductive, but relatively resistive, material, such as a high-resistance heating alloy or a conductive polymer. Sheath 114 is moreover of relatively thin wall construction. A net effect of a high-relative resistance and a thin barrier of such material is to tend to localize current flow in a contact region 120, across a thin layer of resistive material, and limit current flow along the thin layer. Hence, current flow directly across the sheath in region of endothelial contact 120 is favored, and current loss into surrounding blood in a blood-engorged artery, via conduction along a surface of sheath 114, is minimized. In an alternative, optional, realization (not shown), sheath 114 may be of bi-material construction substantially of a non-conductive polymer, with a conductive strip embedded in a region of expected contact with a vessel wall, to allow current transfer.

It should be realized in the preceding discussion that "conductive" and "resistive" and "highly resistive" are relative terms. A "highly-resistive" metal, for example, is considerably more conductive than a semi-conductor, and in general falling in the class of "conductors."

Although the invention has been described in terms of particular embodiments and applications, one of ordinary skill in the art, in light of this teaching, can generate additional embodiments and modifications without departing from the spirit of or exceeding the scope of the claimed invention. As noted above, a rotatable flexible appendage on an intravascular surgical instrument pursuant to the present invention may be made of a material other than metal. In that case, there is no cauterization current passing through the endothelial wall. Instead, the mechanical cutting force of the whipping appendage damages the tissues sufficiently to effectuate permanent vascular collapse.

The flexibility of the appendage may be due to a telescoping capability rather than to a bendability. The key is that the appendage has a variable effective length which adapts to essentially match the distance between tip of the surgical instrument and the inner surface of the blood vessel (or other tubular member) in which the instrument is placed.

Accordingly, it is to be understood that the drawings and descriptions herein are proffered by way of example to facilitate comprehension of the invention and should not be construed to limit the scope thereof.

What is claimed:

1. A medical method for collapsing circulatory vessels in vivo, comprising:
   providing an elongate element having an at least partially flexible appendage attached to a tip of said element;
   inserting said elongate element and said appendage in a circulatory vessel of a patient; and
   simultaneously rotating and withdrawing said elongate element from said vessel, causing said appendage to describe an essentially helical contact path with an inner surface of said vessel, to thereby damage said inner surface and facilitate a permanent collapse of said vessel.

2. The method of claim 1, further comprising passing an electric current from said appendage through a contacting part of said inner surface during the withdrawing of said elongate element from said vessel.

3. The method of claim 2 wherein said appendage includes an outer shell or sheath portion and an inner conductor portion spaced from said outer shell or sheath portion in a stationary state of said appendage, the rotating of said elongate element including bringing said inner conductor portion into contact with an inner side of said outer shell or sheath portion, thereby establishing a current path from said inner conductor portion over said outer shell or sheath portion to said contacting path of said inner surface of said vessel.

4. The method of claim 2 wherein said current is a direct current.

5. The method of claim 2 wherein said current is a pulsed current.

6. The method of claim 1, further comprising providing an elongate sheath enclosing said elongate element and inserting said elongate element in said vessel while the element is substantially enclosed in said sheath.

7. The method of claim 6 wherein said tip of said elongate element is initially enclosed in said sheath, the inserting of said elongate element and said appendage in said circulatory vessel including protruding or ejecting said appendage from said sheath.

8. The method of claim 6 wherein said elongate element is rotated with respect to said sheath during said rotating and substantially fixed axially or longitudinally with respect to said sheath during said withdrawing.

9. The method of claim 1 wherein said appendage has an arcuate form and an internal spring force serving to maintain said appendage in contact with said inner surface of said vessel during the withdrawing and rotating of said elongate element.

10. The method of claim 1 wherein said vessel is a vein, further comprising draining the vein of blood along a target length prior to the withdrawing and rotating of said elongate element.

11. A method of collapsing arteries, comprising:

providing an elongate central conductor having a conductive spring-tail joined to an end of said central conductor;

providing a conductive sheath surrounding said conductive spring-tail and configured to maintain a space between said spring-tail and said sheath free from electrically conductive substances in a mechanically relaxed deployed conformation of said sheath and said spring-tail, said spring-tail and said sheath being also configured to make contact with one another in a region of contact of said sheath with an inner surface of a surrounding vessel or vascular organ;

inserting said central conductor, said spring tail and said sheath into a circulatory vessel of a patient; and generating a potential difference across said spring tail and said inner surface to urge a current flow across said sheath in said region of contact for damaging said inner surface.

12. The method of claim 11, further comprising rotating and withdrawing said central conductor from said circulatory vessel while generating said potential difference.

13. The method of claim 12 wherein said potential difference is a DC potential difference.

14. The method of claim 12 wherein said potential difference is a pulsed potential difference.

15. A surgical device for use in collapsing a blood vessel in a patient, comprising:

an elongate inner shaft;

an elongate outer sheath substantially surrounding said shaft, said sheath being insertable into a circulatory vessel of a patient; and a flexible appendage affixed to a distal tip of said shaft, said appendage being made at least in part of an electrically conductive material, said flexible appendage having an arcuate configuration, said appendage having an internal spring bias tending to spread said appendage into an extended arcuate configuration, said appendage being resilient so as to be temporarily deformable into a different arcuate configuration and so as to resume said extended arcuate configuration after release of said appendage from said different arcuate configuration.

16. A surgical device for use in collapsing a blood vessel in a patient, comprising:

an elongate inner shaft;

an elongate outer sheath substantially surrounding said shaft, said sheath being insertable into a circulatory vessel of a patient; and a flexible appendage affixed to a distal tip of said shaft, said appendage being made at least in part of an electrically conductive material, said flexible appendage having an arcuate configuration, said appendage being a spring-tail wire mounted to a distal tip of said shaft, said wire disposed substantially in a sagittal plane, perpendicular to a longitudinal axis of said shaft.

17. A surgical device for use in collapsing a blood vessel in a patient, comprising:

an elongate inner shaft;

an elongate outer sheath substantially surrounding said shaft, said sheath being insertable into a circulatory vessel of a patient; and a flexible appendage affixed to a distal tip of said shaft, said appendage being made at least in part of an electrically conductive material, said flexible appendage having an arcuate configuration, said appendage including an inner conductive wire and an outer sheath, at least a major portion of said wire being spaced from said sheath in a relaxed configuration of said appendage.

18. An intra-vascular surgical device for the collapse of arteries, comprising:

an elongate shaft, comprising at least a first conductive element;

a spring-tail inner electrode, conductively connected to said first conductive element; and a second conductive element in the form of a conductive sheath, mounted concentrically with and substantially enclosing said shaft, scaled to and electrically isolated from said shaft;

wherein said inner electrode and said sheath constitute an assembly configured to maintain the electrode and the sheath in electrical isolation in a mechanically relaxed configuration of said assembly, but in electrical contact upon sufficient deflection of said assembly from said relaxed configuration by a tissue surface adjacent to and substantially parallel to a longitudinal axis of said shaft, said electrical contact occurring in an immediate vicinity of a touch point of the assembly with said tissue surface.

* * * * *